United States Patent [19]

Boyette et al.

[11] Patent Number: 5,529,773
[45] Date of Patent: Jun. 25, 1996

[54] HERBICIDAL CONTROL OF SICKLEPOD AND COFFEE SENNA WITH *COLLETOTRICHUM GLOEOSPORIOIDES*

[75] Inventors: C. Douglas Boyette, Leland; Jimmy R. McAlpine, Greenville, both of Miss.

[73] Assignee: The United States of America as represented by the Secretary of Agriculture, Washington, D.C.

[21] Appl. No.: 373,177

[22] Filed: Jan. 17, 1995

[51] Int. Cl.⁶ .............................. C12N 1/14; A01N 63/04
[52] U.S. Cl. .................. 424/93.5; 424/93.1; 435/254.1; 504/117
[58] Field of Search .................. 424/93.5, 93.1; 435/254.1; 504/117

[56] References Cited

U.S. PATENT DOCUMENTS

| | | | |
|---|---|---|---|
| 3,849,104 | 11/1974 | Daniel et al. | 424/93.5 |
| 3,997,322 | 12/1976 | Ratledge | 504/225 |
| 4,390,360 | 6/1983 | Walker | 504/117 |
| 4,767,441 | 8/1988 | Walker et al. | 504/117 |
| 4,846,872 | 7/1989 | Kamuro et al. | 504/127 |
| 4,871,386 | 10/1989 | Riley | 424/93.5 |
| 5,221,314 | 6/1993 | Watson et al. | 424/93.5 |
| 5,292,659 | 5/1994 | Cartwright et al. | 504/117 |

OTHER PUBLICATIONS

Brown et al.; Proc. South Weed Sci. Soc. 42:111; 1989.
Elmore; *Proc. South. Weed Sci. Soc.* 42:408–420; 1989.
Boyette et al.; *Weed Science* 27:497–501; 1979.
Mordue; J. E. M. (1971); *CMI Descriptions of Pathogenic Fungi and Bacteria* No. 315.

*Primary Examiner*—Chhaya D. Sayala
*Assistant Examiner*—L. Blaine Lankford
*Attorney, Agent, or Firm*—M. Howard Silverstein; Joseph A. Lipovsky; John D. Fado

[57] ABSTRACT

A strain of the fungus *Colletotrichum gloeosporioides* NRRL 21046 has been discovered, which is herbicidally active against the weeds coffee senna and sicklepod when applied as a postemergent. Compositions of the fungus provide a methodology for a biologically based herbicidal control. This affords an alternative to expensive chemical sprays and thereby a means for protecting the environment.

5 Claims, No Drawings

HERBICIDAL CONTROL OF SICKLEPOD AND COFFEE SENNA WITH *COLLETOTRICHUM GLOEOSPORIOIDES*

BACKGROUND OF THE INVENTION

1. Field of the Invention

The present invention relates to a novel strain of the fungus *Colletotrichum gloeosporioides* possessing herbicidal activity against sicklepod and coffee senna which are weeds endemic to the southern United States, and methods for its use.

2. Description of the Prior Art

Sicklepod (*Cassia obtusifolia* L.) is a major weed problem in much of the southern United States where soybeans and peanuts are grown. This non-nodulating legume is very competitive with these crop plants and can significantly reduce yields at low weed densities. Mature sicklepod plants commonly reach a height of 2 to 2.5 m. The weed produces large quantities of seeds that can germinate and grow under a wide range of environmental conditions. Seedlings characteristically have rounded cotyledons, 15–20 mm across, with 3 to 5 distinct yeins in the upper leaf surface. The first leaves have 3–5 leaflets that are rounded at the tip.

Sicklepod control with herbicides is difficult. An emergency use permit has previously been issued by the United States Environmental Protection Agency (EPA) to allow the use of toxaphene for sicklepod control in soybeans grown in several southern states. Also, metribuzin has been allowed to be applied postmergence directed, but this chemical is sometimes injurious to the soybeans.

Coffee senna (*Cassia occidentalis* L.) is similar in appearance to sicklepod, except that the seed pods are shorter, straighter, and more flattened. It is a non-nodulating leguminous weed in soybean, cotton, and peanut fields in much of the southeastern United States. Although originally introduced as a potential crop, it has escaped cultivation and has become a weed pest. It causes yield loss, seed quality degradation, and difficulty with harvest (Brown et al.; *Proc. South. Weed Sci. Soc.* 42:111; 1989). Control is difficult because of its tolerance to many commonly used herbicides, its prolific growth habit and season-long emergence (Elmore; *Proc. South. Weed Sci. Soc.* 42:408–420; 1989).

The practicality of mycoherbicides for the control of various weeds has been established. U.S. Pat. No. 3,849,104 (Daniel et al.) disclose the control of northern jointvetch with *Colletotrichum gloeosporioides* (Penz.) f. sp. *aeschynomene* (ATCC 20358). Another strain of this fungus, *Colletotrichum gloeosporioides* (Penz.) f. sp. *jussiaeae* (ATCC 52634) has been used to control primrose (Boyette, *Weed Science*, 27: 497–501).

Walker in U.S. Pat. No. 4,390,360 discloses methods for the biological control of multiple weed plants including sicklepod, showy crotalaria, and coffee senna. Control is accomplished by use of a specific host strain of the fungus *Alternaria cassiae* (NRRC 12553) to produce lesions in and kill weeds of these species.

SUMMARY OF THE INVENTION

We have now discovered a new strain of the fungus *Colletotrichum gloeosporioides* that is capable of herbicidally controlling the weeds, coffee senna (*Cassia occidentalis*) and sicklepod (*Cassia obtusifolia*).

In accordance with this discovery, it is an object of the present invention to provide a new microorganism that can be artificially mass-produced and formulated as a herbicide for coffee senna and sicklepod.

It is also an object of the invention to provide a biological alternative to the presently used chemical herbicides.

Another object of this invention is to provide new methods for the herbicidal control of coffee senna and sicklepod.

Other objects and advantages of this invention will become readily apparent from the ensuing description.

DETAILED DESCRIPTION OF THE INVENTION

The fungal pathogen for use herein has been denoted as Colletotrichum gloeosporioides (Penz.) Penz. and Sacc. It was discovered on a greenhouse-grown seedling of coffee senna (*Cassia occidentalis* L.) at the USDA-ARS, Southern Weed Science Laboratory located in Stoneville, Miss. The strain is on deposit with the International Mycological Institute of Egham, Surrey, United Kingdom and assigned accession number: IMI 352028. The strain was also deposited under the identification reference of *Colletotrichum gloeosporioides* on Feb. 1, 1993 with the Agricultural Research Culture Collection (NRRL) in Peoria, Ill. and was assigned accession number: NRRL 21046. This deposit was converted to the terms of the Budapest Treaty on May 23, 1994. The address of the Agricultural Research Culture Collection (NRRL) is: J. L. Swezey, Curator, ARS Patent Collection, Culture Collection Research, NCAUR, 1815 North University Street, Peoria, Ill. 61604.

The morphology Of the isolate is identical to that reported previously for the species by Mordue [J.E.M. (1971) CMI Descriptions of Pathogenic Fungi and Bacteria No. 315]. Spores (conidia) of this fungus are elliptical, with rounded ends, and measure 15–19×4–6 $\mu$; with an average size of 16.5×5.6 $\mu$. The organism produces typical anthracnose lesions on leaves and stems, with acervuli scattered throughout the lesions. The acervuli are glabrous (nonsetose) and are slightly sunken in the host tissue. In moist conditions slimy masses of conidia accumulate on the upper surface of the acervulus breaking the epidermal layer and cuticle. For purposes of this invention, any isolate of this fungus having the identifying characteristics of NRRL 21046, including subcultures thereof, would be effective.

The fungus can be mass-produced and maintained for use by any conventional means. The preferred temperature range for growth is from about 20° C. to about 30° C. with the preferred range being from about 25° C. to about 30° C. The pH should be in the range of about 5.5 to about 7.5 with a preferred range of about 6.0 to about 7.0.

Liquid media were preferable for mass production of spores for greenhouse or field inoculations. Continuous aeration by vigorous shaking was necessary for maximum yields in these media. Highest spore yields ($3\times10^8$ spores/ml) were obtained in 5 days with modified Richard's solution, 500 ml per 2000 ml Erlenmeyer flask, on a rotary shaker (250 RPM) at 25° C. The modified Richard's solution contained 50 g of commercial sucrose, 10 g of $KNO_3$, 5 g of $KH_2PO_4$, 2.5 g of $MgSO_4 \cdot 7H_2O$, 0.02 g of $FeCl_3$, 150 ml of V-8 juice and distilled water to make 1 L; the solution was adjusted to pH 6 with 50% NaOH.

It is envisioned that application of the active agent be done in the form of spraying an aqueous solution on the target plants. Application in the form of a drench to the soil in which the target plants are germinating is another alternative. Concentrations of the conidia to be applied in solution are envisioned to range from about $1\times10^6$ spores/ml to about $1\times10^7$ spores/ml with a minimum concentration of about $1\times10^7$ spores/ml being preferable. The aqueous solutions may be in the form of a water-in-oil suspension with a water:oil ratio ranging from about 1:10 to about 10:1. Useable oils include hydrocarbon or agriculturally based oils with corn oil being preferred.

The following examples are intended only to further illustrate the invention and are not intended to limit the scope of the invention which is defined by the claims.

EXAMPLE I

Spores (conidia) *Colletotrichum gloeosporioides* (Penz.) Penz. and Sacc. [anamorph of *Glomerella cingulata* (Stoneman) Spauld. and Schrenk] was grown in liquid culture of a vegetable juice medium, producing ca. $3\times10^8$ spores per ml after 5 days at 25° C. and 250 rpm. Healthy seedlings (cotyledonary-to-first leaf stage) were inoculated with a distilled water spray containing $1\times10^7$ spores per ml of the fungus. The plants were sprayed until run-off occurred (approximately 3 ml per plant). Control plants were sprayed with distilled water only, at identical rates. Following inoculation, the plants were placed in a dew chamber at 25° C. and 100% relative humidity for 16 hours. The plants were then placed on benches in a greenhouse at 25°–30° C., with 12 hours photoperiods. Typical anthracnose symptoms (dark, elongated, sunken lesions) began forming on stems and leaves within 72 hours after inoculation, and all inoculated plants died within 120 hours after inoculation. Uninoculated plants remained healthy. Weed control was directly proportional to inoculum concentration and plant growth stage at times of inoculation (TABLE I).

TABLE I

Effect of inoculum concentration and plant growth state on biocontrol of coffee senna with *Colletotrichum gloeosporioides*.

| Growth state (No. true leaves) | Inoculum concentration (spores/ml × 10⁶) | | | | | | |
|---|---|---|---|---|---|---|---|
| | 0 | .5 | 1.0 | 1.5 | 2.0 | 5.0 | 10.0 |
| | | | | % Mortality | | | |
| 0–1 | 0 h[1] | 45 e | 82 bc | 100 a | 100 a | 100 a | 100 a |
| 2–3 | 0 h | 20 g | 45 e | 60 d | 75 c | 80 c | 90 bc |
| 4–5 | 0 h | 0 h | 20 g | 25 f | 30 f | 40 e | 50 e |
| >5 | 0 h | 0 h | 0 h | 0 h | 20 g | 25 f | 30 f |

[1]Means followed by same letter do not differ significantly at the 5% level of probability, according to Duncan's multiple range test.

EXAMPLE 2

The effect of dew duration on control of coffee senna and sicklepod (*C. obtusifolia* L.) by the pathogen was tested by placing fungus-inoculated plants in dew chambers for periods of time ranging from 1 to 96 hours. Following the dew treatments, plants were placed on greenhouse benches and observed for 14 days. Only 12 hours of constant dew at 25° C. was required to control coffee senna at 90–98%, while 72 hours of dew was required to control sicklepod at a similar level (TABLE II).

TABLE II

Effect of dew period on biocontrol of coffee senna and sicklepod with *Colletotrichum gloeosporioides*.

| Dew Duration (h) | Mortality[1] | | Biomass Reduction | |
|---|---|---|---|---|
| | Coffee senna | Sicklepod | Coffee senna | Sicklepod |
| | % | | % | |
| 0 | 0 c | 0 f | 0 c | 0 f |
| 1 | 4 e | 0 f | 0 d | 0 f |
| 2 | 6 c | 0 f | 15 d | 0 f |
| 4 | 18 d | 4 f | 30 c | 5 e |
| 6 | 95 c | 6 f | 50 b | 10 c |
| 8 | 90 b | 18 c | 95 a | 22 d |
| 12 | 98 a | 20 c | 99 a | 25 d |
| 16 | 100 a | 20 c | 100 a | 25 d |
| 24 | 100 a | 25 c | 100 a | 28 d |
| 36 | 100 a | 40 d | 100 a | 48 c |
| 48 | 100 a | 58 c | 100 a | 60 a |
| 72 | 100 a | 95 a | 100 a | 100 b |
| 96 | 100 a | 100 a | 100 a | 100 a |

[1]Means within a column followed by the same letter do not differ significantly at the 5% level of probability according to Duncan's multiple range test.

EXAMPLE 3

Aqueous, invert and corn oil formulations of the fungus were tested for their efficacies in controlling coffee senna and sicklepod. Seedlings of each species (cotyledonary-to-first leaf stage) were inoculated by spraying until total leaf and stem wetness occurred with one of the following treatments: 1) fungal spores/water; 2) fungal spores/invert[1]; 3) fungal spores/corn oil[2] (1:1 spores in water:corn oil); 4) water only; 5) invert only; 6) corn oil only (1:1 water:corn oil). Following inoculations, the plants were placed in a dew chamber at 25° C. for 16 hours, removed, placed on greenhouse benches and observed for disease development for 14 days.

[1]The oil phase of the invert used in this report, designated MSG-8.25P consisted of: paraffinic oil (Orchex 796, Exxon Corp., Baytown, Tex. 77520) at 777 g L-¹; monoglyceride emulsifier (Myverol 18-99, Eastman Chemical Products, Inc., Kingsport, Tenn. 37662) at 14.5 g L-¹; paraffinic wax (Gulfwax, American Home Products Corp., New York, N.Y. 10017) at 74.25 g L-¹; and lanolin (Fisher Scientific, Pittsburgh, Pa. 15219) at 93 g L-¹. The wax and monoglyceride were dissolved in warm (60° C.) paraffinic oil. To prepare the emulsion, distilled water containing *C. gloeosporioides* conidia was added at a ratio of 2:3 (v/v) water+conidia: MSG-8.25 oil phase, and stirred briskly for 60 seconds. (Quimby, P. C., Jr. 1990. Control of Undesirable Vegetation. U.S. Pat. No. 4,902,333).
[2]Spectrum Natural Expeller Pressed Corn Oil, Spectrum Marketing Corp., Petaluma, Calif. 94952.

Disease symptoms began occurring on both coffee senna and sicklepod within three days after inoculation with the fungus/invert and fungus/corn oil treatments. After 14 days, 60% and 85% mortality occurred to sicklepod treated with the fungus/invert and fungus/corn oil treatments, respectively, while these same treatments controlled coffee senna 85% and 95%, respectively (TABLE III).

TABLE III

Effect of formulation of *Colletotrichum gloeosporioides* on biocontrol of coffee senna and sicklepod.

| Treatment | Mortality[1,2] | | Biomass Reduction | |
|---|---|---|---|---|
| | Coffee senna | Sicklepod | Coffee senna | Sicklepod |
| Spores/H$_2$O | 100 a | 10 c | 100 a | 20 b |
| Spores/Invert | 60 b | 85 b | 96 a | 80 a |
| Spores/corn oil | 85 a | 95 a | 98 a | 90 a |
| H$_2$O only | 0 c | 0 d | 0 b | 0 c |
| Invert only | 0 c | 0 d | 10 b | 12 b |
| Corn oil only | 0 c | 0 d | 8 b | 10 b |

[1]All plants were subjected to a 16 hour dew treatment at 25° C.
[2]Means within a column followed by the same letter do not differ significantly at the 5% level of probability according to Duncan's multiple range test.

EXAMPLE 4

Seedlings of various crop and weed species were inoculated with aqueous fungal sprays, as described in EXAMPLE 1, and subjected to 16 hours of dew at 25° C. Following dew treatments, the plants were placed on greenhouse benches and observed for 21 days. Of the plants that were inoculated with the fungus, only coffee senna and sicklepod were visibly affected, with coffee senna exhibiting much greater susceptibility to the fungus than sicklepod (TABLE IV).

TABLE IV

Reaction of various plant species to foliar sprays of *Colletotrichum gloeosporioides*.

| FAMILY Common Name, Scientific Name, Cultivar | Disease Reaction[a] |
|---|---|
| COMPOSITAE | |
| Cocklebur (*Xanthium strumarium* L. #XANST) | NS |
| CONVOLVULACEAE | |
| Morningglory (*Ipomoea* spp.) | NS |
| CUCURBITACEAE | |
| Pumpkin (*Cucurbita pepo* L.) | NS |
| 'Jack-O-Lantern' | |
| Squash [*Cucurbita pepo* var. *melopepo* (L.) Alef.] | NS |
| 'Golden Summer Crookneck' | |
| Watermelon (*Citrullus vulgaris* Schrl.) | NS |
| 'Charleston Grey' | |
| GRAMINAE | |
| Corn (*Zea mays* L.) | NS |
| 'Truckers Favorite' | |
| Johnsongrass [*Sorghum halepense* (L.) Pers. #SORHA] | NS |
| Rice (*Oryza sativa* L.) | |
| 'LaBelle' | NS |
| 'Starbonnet' | NS |
| Grain sorghum (*Sorghum bicolor* (L.) Moench) | NS |
| 'Texas C-124' | |
| LEGUMINOSAE | |
| Alfalfa (*Medicago sativa* L.) | NS |
| 'Delta' | |
| Coffee senna (*Cassia occidentalis* L. #CASOC) | HH |
| Sicklepod (*Cassia obtusifolia* L. #CASOB) | SS |
| Florida beggarweed (*Desmodium tortuosum* #DEDTO) | NS |

TABLE IV-continued

Reaction of various plant species to foliar sprays of *Colletotrichum gloeosporioides*.

| FAMILY Common Name, Scientific Name, Cultivar | Disease Reaction[a] |
|---|---|
| Showy crotalaria (*Crotalaria spectabilis* L. #CVTSP) | NS |
| Hemp sesbania [*Sesbania exaltata* (Raf.) Cory #SEBEX] | NS |
| Rattlebox (*Sesbania drummondii* L. #SEBDR) | NS |
| Northern jointvetch (*Aeschynomene virginica* (L.) B.S.P. #AESVI] | NS |
| Soybean [*Glycine max* (L.) Merr.] | NS |
| 'Bedford' | NS |
| 'Bragg' | NS |
| 'Dare' | NS |
| 'Davis' | NS |
| 'Forrest' | NS |
| 'Hill' | NS |
| 'Hood' | NS |
| 'Contennial' | NS |
| 'Tracy' | NS |
| Peanut (*Arachis hypoqoea* L.) | NS |
| 'Tennessee Reds' | |
| Garden bean (*Phaseolus vulgaris* L.) | |
| 'Kentucky Wonder' | NS |
| 'Romano Pole' | NS |
| 'Ohio Pole' | NS |
| 'Jackson Wonder' | NS |
| 'Henderson Bush Lima' | NS |
| 'Lady Cowpea' | NS |
| 'White Crowder Pea' | NS |
| MALVACEAE | |
| Cotton (*Gossypium hirsutum* L.) | |
| 'Stoneville 213' | NS |
| 'Deltapine 61' | NS |
| Prickly sida (*Sida spinosa* L. #SIDSP) | NS |
| Velvetleaf (*Abutilon theopharasti* Medic. #ABUTH) | NS |
| SOLANACEAE | |
| Tomato (*Lycopersicon esculentum* Mill) | |
| 'Beefsteak' | NS |
| 'Marion' | NS |
| Jimsonweed (*Datura stramonium* L. #DATST) | NS |

[a]NS = No visible disease symptoms.
SS = Slightly Susceptible; small (<2 mm) lesions; fungus sporulated on necrotic tissue; plants outgret symptoms.
HH = Highly Susceptible; severe necrosis; lesion coalescence; all or most inoculated plants killed.

We claim:

1. A biologically pure culture of *Colletotrichum gloeosporioides* having all the identifying characteristics of strain NRRL 21046, being capable of herbicidally controlling coffee senna and sicklepod.

2. A biologically pure culture of *Colletotrichum gloeosporioides* strain NRRL 21046 or subcultures thereof which are capable of herbicidally controlling coffee senna and sicklepod.

3. A method of herbicidally controlling coffee senna comprising applying a herbicidally effective amount of *Colletotrichum gloeosporioides* strain NRRL 21046 to the plant.

4. The method of claim 3 wherein *Colletotrichum gloeosporioides* is sprayed on the plant at a minimum concentration of $1 \times 10^7$ spores per milliliter.

5. The method of claim 3 wherein the *Colletotrichum gloeosporioides* is applied in the form of a water-in-oil formulation.

* * * * *